(12) United States Patent
Turcotte (10) Patent No.: US 6,818,177 B1
(45) Date of Patent: Nov. 16, 2004

(54) ULTRAVIOLET AIR PURIFICATION SYSTEMS

(76) Inventor: Mark Turcotte, 27022 Jarvis Rd., Bonita Springs, FL (US) 34135

( * ) Notice: Subject to any disclaimer, the term of this patent is extended or adjusted under 35 U.S.C. 154(b) by 452 days.

(21) Appl. No.: 09/708,709

(22) Filed: Nov. 9, 2000

Related U.S. Application Data (60) Provisional application No. 60/187,008, filed on Mar. 6, 2000, and provisional application No. 60/164,337, filed on Nov. 9, 1999.

(51) Int. Cl.$^7$ ................................................ A61L 2/00
(52) U.S. Cl. .................... 422/24; 250/435; 250/436; 250/455.11; 96/226; 99/224; 422/120; 422/121; 422/105
(58) Field of Search .................. 422/24, 121, 120, 422/105; 250/455.11, 435, 436; 99/224; 96/226

(56) References Cited

U.S. PATENT DOCUMENTS

| | | | | |
|---|---|---|---|---|
| 4,017,736 A | | 4/1977 | Ross ........................... 250/435 |
| 4,210,429 A | | 7/1980 | Golstein ...................... 55/279 |
| 4,786,812 A | | 11/1988 | Humphreys .............. 250/455.1 |
| 4,806,768 A | | 2/1989 | Keutenedjian .............. 250/436 |
| 4,931,654 A | | 6/1990 | Horng ......................... 250/436 |
| 4,990,313 A | * | 2/1991 | Pacosz ........................ 422/121 |
| 5,112,370 A | | 5/1992 | Gazzano ...................... 55/102 |
| 5,225,167 A | | 7/1993 | Wetzel ........................ 422/121 |
| 5,330,722 A | | 7/1994 | Pick et al. ................... 422/121 |
| 5,453,049 A | | 9/1995 | Tillman, Jr. et al. ........ 454/228 |
| 5,492,557 A | | 2/1996 | Vanella ........................ 96/16 |
| 5,505,904 A | | 4/1996 | Haidinger et al. ............ 422/24 |
| 5,523,057 A | | 6/1996 | Mazzilli ...................... 422/121 |
| 5,558,158 A | | 9/1996 | Elmore ........................ 165/122 |
| 5,601,786 A | | 2/1997 | Monagan ..................... 422/108 |
| 5,612,001 A | | 3/1997 | Matschke .................... 422/121 |
| 5,616,172 A | | 4/1997 | Tuckerman et al. ............ 96/16 |
| 5,635,133 A | | 6/1997 | Glazman ...................... 422/24 |
| 5,656,242 A | | 8/1997 | Morrow et al. .............. 422/131 |
| 5,742,063 A | | 4/1998 | Scroggins et al. ...... 250/455.11 |
| 5,759,239 A | | 6/1998 | Yu .................................. 96/3 |
| 5,817,276 A | | 10/1998 | Fencl et al. .................... 422/24 |
| 5,833,740 A | | 11/1998 | Brais ............................. 96/16 |
| 5,837,207 A | | 11/1998 | Summers ..................... 422/121 |
| 5,866,076 A | | 2/1999 | Fencl et al. .................. 422/121 |
| 5,894,130 A | | 4/1999 | Bach ........................... 250/436 |
| 5,902,552 A | | 5/1999 | Brickley ...................... 422/121 |
| 5,997,619 A | | 12/1999 | Knuth et al. .................. 96/224 |
| 6,280,686 B1 | * | 8/2001 | Scheir et al. .................. 422/24 |

* cited by examiner

*Primary Examiner*—Krisanne Jastrzab
(74) *Attorney, Agent, or Firm*—Morrison & Foerster LLP (57) ABSTRACT

The present invention relates to ultraviolet air purification devices and custom component kits useful residential and commercial settings. Apparatus and kits according to the invention include an electrical control relay, a safety switch, and a separate ballast for each lamp. When multiple lamps are used, a suppressor ballast is used to protect the lamps from electrical surges. Terminal strips are included so multiple ballasts and lamps can be used as part of the electrical configuration. The invention allows for UV-C bulbs and is designed so that only the lamps and their connectors must be disposed in the path of the air flow. The lamps are easily installed by pushing into a connector on one end. Supports for the end and the middle of the bulbs may be used in installation. LED indicator lights show if each lamp is receiving the electrical charge. Multi-faceted tin reflectors may be installed on each end.

42 Claims, 9 Drawing Sheets

TYPICAL RESIDENTIAL LAMP IN DUCT PLACEMENT

ULTRAVIOLET AIR PURIFICATION SYSTEMS

REFERENCE TO RELATED APPLICATIONS

This application claims the benefit of U.S. Provisional Patent Application Ser. No. 60/164,337, entitled Customized Commercial Ultraviolet Air Purification Kit, filed Nov. 9, 1999, and U.S. Provisional Patent Application Ser. No. 60/187,008, entitled Customized Commercial Ultraviolet Air Purification Kit, filed Mar. 6, 2000.

BACKGROUND OF THE INVENTION

1. Field of the Invention

This invention relates to methods for purifying the air, and more specifically, to systems and methods for purifying air using ultraviolet radiation that are easily customized to accommodate different air handling systems, allow for remote location of certain components and provide superior purification levels.

2. Description of the Background

Ultraviolet (UV) germicidal irradiation has been known by scientist for over 80 years to kill fungi, bacteria, virus and other contaminants. These contaminants can pose a health hazard in buildings and other enclosed environments, and have been linked to Sick Building Syndrome and Building Related Illness, among other conditions.

A number of different systems have utilized ultraviolet radiation in order to improve air quality. Some devices are designed for use in large air handling systems while others are used to purify air on a smaller scale, such as in a single room. For example, with respect to purifying airflow in an air conditioning systems, U.S. Pat. No. 5,742,063, relates to an air sanitizer attachment which can be mounted on the top of a small air duct. The sanitizer has an aluminum housing and at least one UV emitting probe having a single ended-double tube design extending vertically downward into the duct. A light sensor allows for a determination of whether the probe is on without having to remove the device or be exposed to UV radiation. The inside of the ducts may be lined with reflective material and the entire device, including the ballast, is mounted on the top of the air duct to which it is attached.

U.S. Pat. No. 5,866,076 relates to a single-ended germicidal lamp for HVAC systems that is also mounted on the duct wall. A 110V, 60 Hz ballast is used to drive the UV tube and a mounting mechanism with a spring clamp and gaskets absorbs shock and vibration to the tube.

U.S. Pat. No. 5,817,276 relates to a method of UV distribution in an air handling system for surface and air sterilization. According to this patent, the system coil and drain pan components are subjected to UV-C radiation, to kill mold and bacteria growing on the coil and drain pan. A germicidal lamp in the form of a substantially linear germicidal tube is mounted in the air duct, with the lamp base mounted inside or on the outside of the duct and a reflector incorporated in the base.

U.S. Pat. No. 5,894,130 relates to an ultraviolet sterilization unit for use in forced air heating and cooling systems. This device is designed to insure the lamps are turned off to prevent unwanted exposure to UV radiation. The unit is mounted on a duct, such as the duct for the cool air return.

U.S. Pat. No. 5,523,057 relates to an air sterilization and filtration apparatus that can be installed in an air conditioning system. This device has an activated carbon filter and a remote power supply pack that activates the ultraviolet lights only when there is air movement in the ventilation system. A tackified first filter filters the air before it passes into a reflective chamber containing a plurality of ultraviolet lamps which then passes through an activated carbon filter. The system may be attached to the air intake chamber of a residential system or may be placed inside duct work. In addition, a post germicidal lamp may be positioned downstream of a wet coil to destroy bacteria on the wet coil.

U.S. Pat. No. 5,558,158 relates to a hygienic air handler that uses ultraviolet light downstream from the heat exchanger in a highly reflective chamber to discourage microorganisms. According to this patent, the end mounts for the UV sources are disposed inside the air handler and are fastened to the walls.

U.S. Pat. No. 5,833,740 relates to an air purifier having a turbulence generator and UV lamp tubes disposed in a reflective housing. This device is useful in the air return plenum of any system. U.S. Pat. No. 5,902,552 relates to an ultraviolet air sterilization device in which a housing and one or more mounts connect to germicidal lamps via 120V, 0.3 amp ballast. The device is mounted on the air handling duct so that the lamps protrude into the air stream of the duct.

A number of other devices have been described as being useful in either a room air application or as part of an air conditioning system. For example, U.S. Pat. No. 5,656,242 relates to an air purifier comprising a blower, porous air filters, a plurality of ballast or RF powered UV lamps disposed in a primary radiation zone and an electrostatic filter element (electrically charged grid). A reflective member/reflective walls are used to enhance irradiation in the primary irradiation zone. The purifier may be used to purify room air, or be modified for incorporation into a heating furnace.

U.S. Pat. No. 5,112,370 relates to a device for sterilizing a forced air flow using ultraviolet radiation. An elongated housing with reflecting inner surfaces accommodates an ultraviolet radiation source. A fan for drawing in and sending out air may be used or, alternately, the device may be fitted inside the output duct of an air conditioner. In the latter embodiment, three lamps are contained in a relatively short housing. The inner surface of the housing is black or dark-coated in order to absorb radiation. U.S. Pat. No. 5,837,207 relates to a portable germicidal air filter for home use incorporating an electrostatic air filter, an ultraviolet lamp and an oscillating parabolic reflector or lens for focusing the ultraviolet radiation on an upstream side of the air filter.

A number of devices are optimized to purify smaller volumes of air, such as the air in a single room. For example, U.S. Pat. No. 5,997,169 relates to a self-contained room air purification system having a first filter (comprising a particulate pre-filter, an intermediate carbon filter and an innermost HEPA filter), UV germicidal lamps and a downstream carbon mesh filter. The device is portable and can be wheeled into a room.

U.S. Pat. No. 4,017,736 relates to a portable or stationary air purification system which uses a two stage filter (consisting of a pre-filter metal mesh and a submicron laminar flow cell) in connection with a high intensity ultraviolet generator to kill microorganisms. According to this patent, a fan is used to force air through a shielded enclosure. U.S. Pat. No. 4,210,429 relates to a free-standing room air purifier that incorporates UV lamps and three separate filters (a prefilter in the inlet of the blower, a main filter element vertically stacked over the blower and lamps, and a charcoal filter disposed over the main filter element). In this device, a blower draws air into the housing and fifteen-watt germicidal lamps (General Electric part No. G15T8) are disposed inside the housing.

U.S. Pat. No. 4,786,812 relates to a portable germicidal machine which uses a plurality of ultraviolet light bulbs useful to purify room air and surfaces. The ultraviolet bulbs are disposed in a housing which has an open lower end covered with a grate. A reflective surface and fan is provided above the bulbs to draw air upward into the machine. In operation, air flows through a filter into the light chamber. Semicircular reflecting shields have holes through them to allow air flow. Bacteria on surfaces beneath the device and in air passing over the surface are killed by direct and reflected ultraviolet radiation as the device passes over the surface.

U.S. Pat. No. 4,806,768 relates to an air purifying apparatus useful in a home, office, industrial plant or hospital setting to degrade microorganisms and allergens. In this device, infrared and ultraviolet lamps are disposed in a casing having an inlet and an outlet. The infra-red light is used to heat the microorganisms to make them more susceptible to UV radiation. U.S. Pat. No. 4,931,654 relates to a radiant air sterilizing and filtering apparatus. The radiant sterilizing means (UV light source) is moveable so that it may either be enclosed in the housing or extended outward from the housing. Heating means may be provided in the housing adjacent the air inlet, and filters may be provided at the air inlet and outlet. A fan is mounted on the bottom wall to draw air into the housing. Reflectors are provided on the inner wall of the housing.

U.S. Pat. No. 5,225,167 relates to a room air sterilizer that mounts on the wall of a room and traps airborne particulate in a HEPA filter. The HEPA filter is disposed near the outflow port. A blower in the housing moves air from the intake port to the outflow port. An ultraviolet germicidal lamp disposed on the intake side of the filter destroys biocontaminants on the particulates. A prefilter may be disposed below the blower and a second UV lamp below the prefilter may be used to expose the inflow side to ultraviolet radiation. U.S. Pat. No. 5,330,722 relates to a portable air purification system using filtration and ultraviolet radiation. In this device, the filter and UV light source are moveable with respect to one another, allowing controlled irradiation of the filter surface. U.S. Pat. No. 5,453,049 relates to a corner air filtration unit designed to fit in a corner of a room, using HEPA or ULPA filters. An ultraviolet lamp may optionally be mounted in the housing.

U.S. Pat. No. 5,612,001 relates to a germicidal room air cleansing apparatus having an ellipsoid chamber formed of reflective material. UV lamps are disposed in the chamber to cleanse the air. U.S. Pat. No. 5,616,172 relates to a self-contained portable air treatment system that uses prefilters, UV lamps and a HEPA filter to purify room air.

U.S. Pat. No. 5,492,557 relates to a filter device for air purification having an electrification grid to negatively charge particles, a positively charged collector plate for attracting the negatively charged particles, and a UV lamp disposed near the collector plate to illuminate the entire length of the plate. U.S. Pat. No. 5,505,904 relates to an air disinfection unit in which air is directed past a plurality of closely spaced UV-C bulbs producing UV-C irradiation at an intensity of about 142 $\mu W/cm^2$.

U.S. Pat. No. 5,601,786 relates to an air purifier that uses ultraviolet radiation at two different energy intensities, i.e. ozone generating and germicidal wavelengths, to purify the air. U.S. Pat. No. 5,635,133 relates to an apparatus for killing microorganisms in a fluid medium, such as air or liquid, using filters, UV radiation and parabolic reflectors. U.S. Pat. No. 5,759,239 relates to a flat, compact air purifier which uses static electricity and metal wire gauze filters, magnetic elements and sterilizing lamps to purify the air.

A primary source of the contaminants in the circulating air comes from contaminants that accumulate on the cooling coils in the system. Efforts to eliminate these hazards has led to increased costs, particularly in commercial settings, for air handler coil cleaning. Because of the huge size and particularly the depth of cooling coils in commercial and similar settings, the cooling coil often reaches a point where it can no longer be effectively cleaned. Many coils are 12" thick or more; after a period of years the center of those coils cannot be easily reached for cleaning. Further, UV units are often placed on one side of a cooling coil such that only one side can be effectively cleaned. As a result, the coils must be removed and either replaced or subjected to a chemical dip. Such procedures are time consuming and costly.

Ultraviolet devices currently used in connection with large air handling systems to eliminate contaminants are limited in their ability to efficiently and completely clean the entire coil. In addition, current devices must be custom-made for individual cooling systems. These devices are costly to design and maintain. In addition, devices that are disposed inside the duct of an air conditioning system are prone to increased wear and deterioration due to vibration and conditions inside the system.

Consequently, there is a need for an effective and durable purification system that is easily adapted for air handling systems of differing configurations, that is useful to clean both the air circulating in the system as well as the cooling elements themselves.

SUMMARY OF THE INVENTION

The present invention overcomes the problems and disadvantages associated with current strategies and designs and provides a purification apparatus that can be used to purify circulating air and also clean the cooling coils of an air conditioning system. The device is useful in both residential and commercial settings.

One embodiment of the invention is directed to apparatus for killing microorganisms in an air conditioning system. Apparatus are particularly useful for either commercial or residential systems. In a commercial setting, the apparatus may have a plurality of ballasts (e.g. 16 or more) such that the apparatus may further comprise a suppressor ballast coupled to a control relay for suppressing any electrical surge when the apparatus is activated, a plurality of fluorescent light ballasts coupled to the suppressor ballast, the fluorescent light ballasts configured to convert 60 hertz to 20–100 kilohertz, a plurality of four pin electrical connectors, wherein each of the plurality of four pin electrical connectors is coupled to one of the plurality of fluorescent light ballasts and is adapted to receive a UV-C lamp, means for de-energizing the lamps in response to a signal change, and indicator means for indicating when one or more of the plurality of lamps are energized. The four pin electrical connectors are preferably coupled to the fluorescent light ballasts via coupling means such as, for example, via wire leads from the ballast, of sufficient length that the four pin electrical connectors and UV lamps may be disposed inside an air conditioning duct, remote from the control relay, the suppressor ballast and the fluorescent light ballasts. The apparatus may further comprise a plurality of UV-C lamps designed for mating with the four pin electrical connectors and a plurality of reflectors arranged so that a reflector is disposed at at least one end of each lamp. The connectors, lamps and reflectors are preferably disposed inside the duct such that the reflectors spin as air flows through the duct. The apparatus may further comprise a safety switch, such as a ⅞"×1¾" Edward's brand or a high voltage push button with normally open contacts with fast make and break regardless of how pressure is applied or released having a rugged construction of phosphor bronze, self cleaning contacts that withstand shock and vibration insulated protective sleeves, locknut-type, UL recognized complete with ½" locknut/flexible No. 16 gauge wire leads, and 3" long heavy duty shell chrome plated. At 120 volts the contact ratings are 6.0 AC amps and 3.0 DC amps. At 250 volts the contact ratings are 3.0 AC amps and 1.0 DC amps.

Another embodiment of the invention is directed to kits comprising customized air purification devices that each comprise one or more of a cover, a control relay, a safety switch, an optional suppressor ballast, a plurality of fluorescent lamp ballasts, a plurality of terminal strips, a plurality of LED indicator lights, a plurality of four pin electrical connectors, and one or more components selected from the group consisting of a plurality of UV-C lamps, a plurality of connecting wires, a plurality of multi-faceted tin reflectors, a reflective tape, a free-standing stand, a plurality of self tapping aluminum screws, a plurality of UV-C lamps, a plurality of concrete screws and a Plexiglas door.

Another embodiment of the invention is directed to methods for killing microorganisms in an air conditioning system having at least one duct for the passage of air there through, the method comprising providing connecting means for connecting to a main power source, providing a suppressor ballast coupled to the connecting means for suppressing any electrical surge when the apparatus is activated such as when 16 or more ballasts are being used, providing a fluorescent light ballast coupled to the suppressor ballast, the fluorescent light ballast configured to convert 60 hertz to 20–100 kilohertz, providing an electrical connector, coupled to the fluorescent light ballast and adapted to receive a UV-C lamp, and wherein the electrical connector is coupled to the fluorescent light ballast via coupling means such that the electrical connector may be disposed remote from the connecting means, the optional suppressor ballast and the fluorescent light ballast, providing means for de-energizing the lamp in response to a signal change, and providing indicator means for indicating when the lamp is energized.

Other embodiments and advantages of the invention are set forth in part in the description which follows, and in part, will be obvious from this description, or may be learned from the practice of the invention.

DESCRIPTION OF THE DRAWINGS

FIG. 1 is a schematic of a purification system including (a) a lamp and ballast design, (b) a door design, (c) a four plug design, and (d) a side view.

FIG. 2 is a schematic of an apparatus for commercial use showing (a) a ballast design, and (b) a lamp design.

FIG. 3 is a schematic showing (a) placement of a lamp holder in a duct, (b) a side view of the lamp holder, and (c) a front view of a lamp holder.

FIG. 4 is a schematic of an apparatus for residential use showing (a) a design of the outer unit and (b) a design of the inner unit.

DESCRIPTION OF THE INVENTION

As embodied and broadly described herein, the present invention is directed to air purification devices and kits for installing a customized ultraviolet air purification device. Devices according to the invention can be used in all settings including both commercial and residential. The present invention is a substantial improvement over existing devices that are currently available for use in either commercial or residential settings. The existing devices are expensive due to custom manufacturing requirements and, consequently, can also be difficult to customize. The invention is designed to eliminate mold, mildew, bacteria and viruses, or otherwise render these contaminants ineffective to cause disease. The invention purifies air passing by the lamps and also neutralizes stationary contaminants within the effective radius of the lamp and further allows for the disinfection and purification of air as that air travels past the UV lamps.

Ultraviolet devices of the invention have the power to irradiate not only the air but also the coil. The coil is cleaned all the way through, and kept clean, thus avoiding costly replacement. Further, existing devices, although somewhat effective, may still permit mold to grow towards the bottom of the coil. The present invention eliminates this problem by providing, among other things, a multi-faceted reflector at the end of each bulb. In addition, existing devices are generally mounted directly on the air duct or within the duct, subjecting the purification unit to increased vibration and deterioration of the unit. The present invention provides a free-standing option with respect to the electrical components of the device, such as the ballasts, and provides designs which allow most of the components of the system to be disposed remotely (for example using connecting wires) from the ducts of the air conditioning system. These options eliminate much of the vibration that causes deterioration of existing devices.

Further, a suppressor ballast may be used with multiple bulbs to interrupt the power surge related to turning the unit on or powering up the unit. Powering up the unit with more than, for example, fifteen ballasts hold a large potential for destroying UV lamps. The suppressor allows the electrical current to be interrupted for a microsecond at a time until full electrical power is completed to all ballasts. Also, existing devices incorporate varying amounts of plastic. When these plastic components are exposed to UV, as well as other components of the system, they deteriorate over time. The kits of the present invention include reflective tape to protect these and existing components of the apparatus and the overall system from exposure to the UV radiation.

As many components are expected to be similar and often identical between units, kits can be created by a manufacturer which can be standardized for similar use or individually customized. The kit form of the invention also allows the building owner/contractor to customize the purification system to meet the specific needs in the field according to the individual nature of the air conveyance system and the needs of the job. The kit includes all the components necessary to construct a customized device for purifying the air, including an electrical control relay, a safety switch, a suppressor and a separate ballast for each lamp. The kit form is particularly useful to accommodate the customized nature of most commercial air conveyance systems.

Devices according to the invention allow for easy replacement of lamp bulbs as, preferably, there is an electrical connection on only one end of the long bulb. Further, the invention design allows for an enhanced cleaning ability. For example, conventional designs and the designs of the invention allow for cleaning utilizing one lamp per ballast. The invention design also allows for cleaning using dual lamp per ballast by placing one lamp on each side of the coil. For an air handler designed to fit 20 lamps at the coil, the invention allows for the use of 40 lamps (20 for each side of the coil) thus allowing for cleaning of the entire coil plus the blower wheel which moves air through the air handler and is susceptible to the growth of mold and fungi. In addition to maintaining the cleanliness of the air conditioning system, the unit of the invention utilizes a high amount of UV to clean the air which is accomplished by engineering the amount of UV to be provided to the system. Engineering can involve a formula that takes in account (i) the cubic feet per minute moved through the air handler, (ii) the height of the duct, (iii) the width of the duct, (iv) the length of the duct, and (v) the temperature of the air.

The present invention allows for the installation within an air conveyance system (ductwork, etc.) of a number of ultraviolet bulbs emitting UV-C rays (in the range of 200–280 nanometers), which are hooked to an externally installed electrical ballast (one for each bulb or one ballast for every two lamps), and an optional, special electric suppressor ballast which delays the electrical impulse (when the units are turned on) so that the surge of electricity does not burn out the bulbs. The suppressor also provides a distinct advantage compared to conventional designs. For example, in existing devices, multiple bulbs are subject to being blown with the first electrical surge. The use of the suppressor according to the invention allows for the use of bulbs but avoids the problem caused by surges.

Novel features of the invention also include multi-faceted reflectors on each end of the bulb. These reflectors may spin with air flow in the air conveyance system. A reflective interior can increase UV intensity up to 300%. In addition, the invention provides for LED light readouts for each lamp or ballast which runs a set of lamps.

In a preferred embodiment, ducts may be covered with reflective material to maximize the effectiveness of the UV radiation. The reflective material may be the composition of the ducts themselves, a reflective plating, a reflective coating or lamination of, for example, tape or paint, or a combination of these measures. One preferred embodiment is to coat the ducts with aluminum paint. Aluminum has a high reflectancy value for UV and is both easy to use and apply to most any surface. Aluminum paint is commercially available as Sherwin Williams Silver-Brite Aluminum paint which has a heat reflective/dry heat resistance to 400 degrees F., and UV resistance when applied at a thickness of no greater than 1.5 mils dft/ct.

Alternately, an aluminum coil stock may be used to enhance reflection. For example, aluminum coil stock can be rolled out, and cut to fit and installed in the portion of the duct surrounding the UV apparatus. The aluminum may be fastened, for example, with a spray contact cement and a rivet/grommet combination.

Further, the present invention provides for a free-standing part of the electrical device. In existing devices, all components (bulb and electrical) are mounted to or in the air handler. This subjects the ballasts to years of wear and tear from vibration. In contrast, the ballasts of the present invention do not have to be attached to the air handler. Thus, devices of the present invention last longer as they are not subject to the vibration of huge walk-in-size air handlers.

Figure 1A:
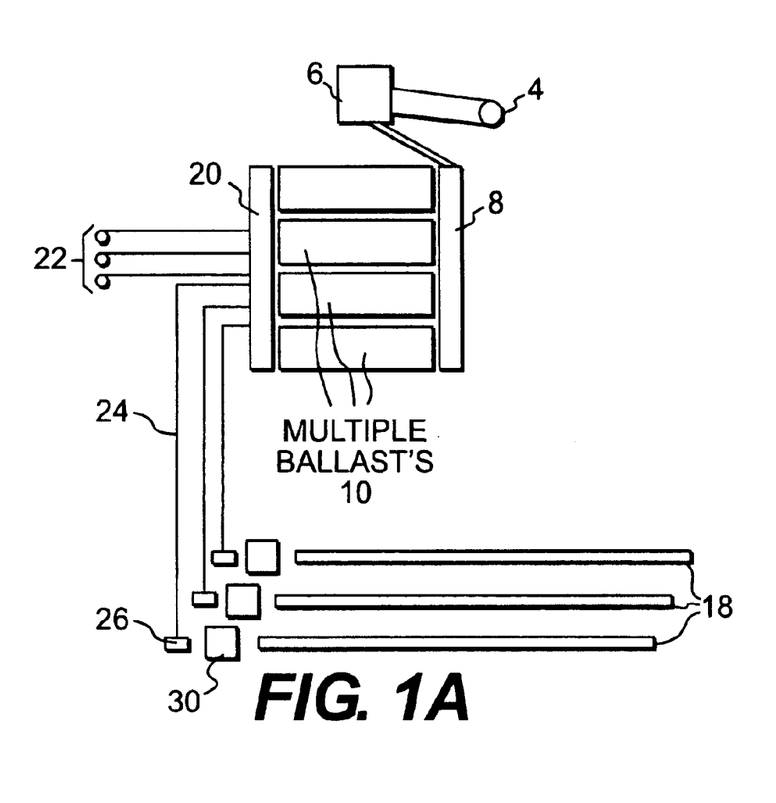
Figure 1B:
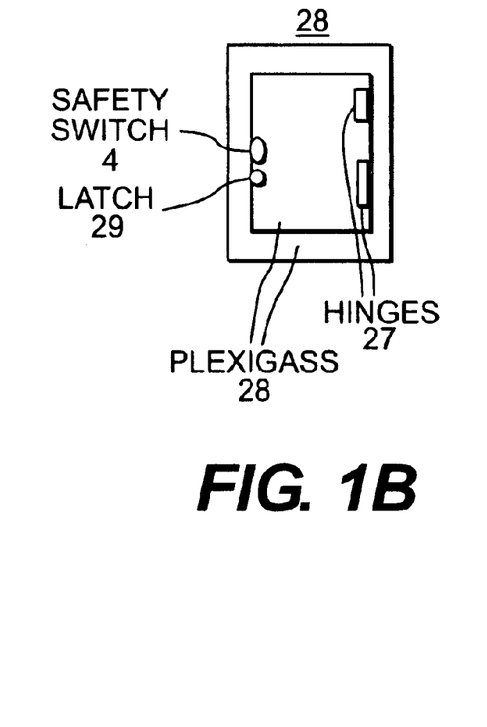
Figures 1C, 1D:
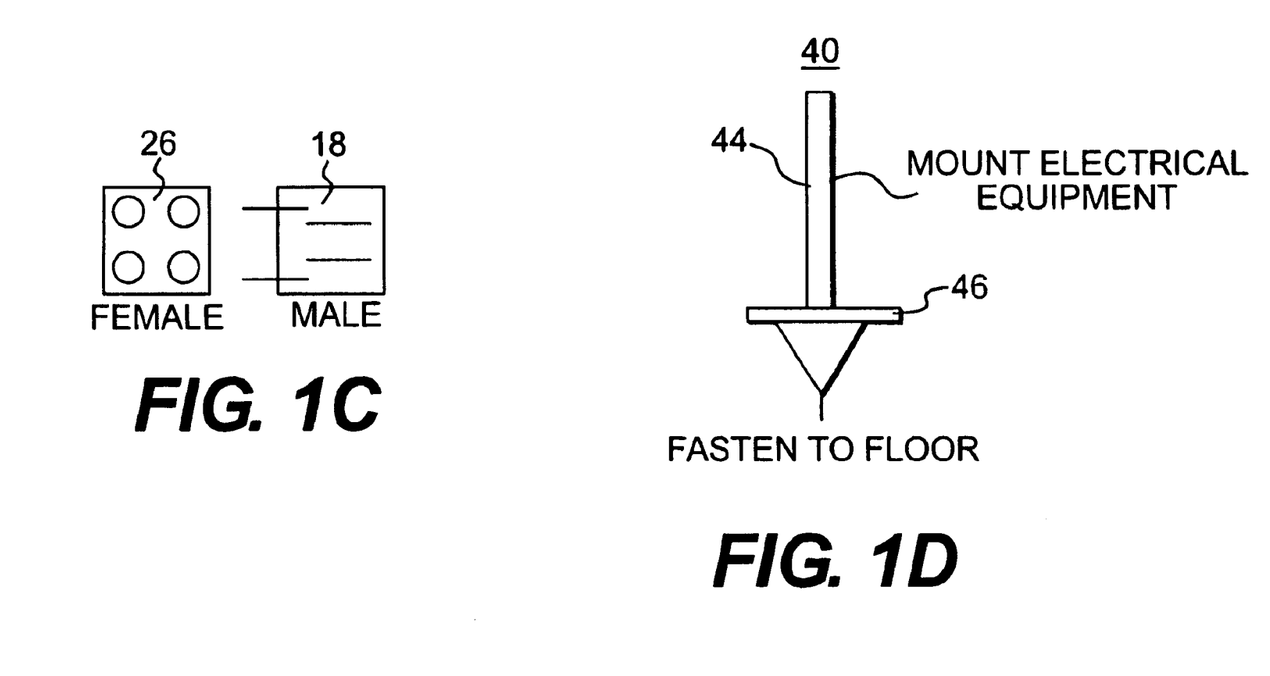

A preferred embodiment of the invention is depicted in FIG. 1, which can be custom designed for each individual system based on numerous factors, can be provided as a complete and ready to install unit; Purification device 1 is preferably designed for use with most any ballast such as a worldwide market ballast which is a ballast that automatically accept currents ranging from 120V through 240V and all voltage in between (ballasts run at 60 hertz in the U.S. and 50 hertz which is common elsewhere). This design gives the flexibility to use for the common applications of 120v and 240V and is excellent for overseas applications in areas which have brown out problems or a reduction in electrical current that vacillates thus causing a burning out of ballasts. Since this ballasts automatically detects changing currents it is able to stay operational and is protected from the changing current (120v to 240v high voltage momentary contact safety switch). Suppressor ballasts are generally used with 16 or more lamps to prevent lamp harm and lamps may be standard or high output types. All these ballast have similar features such as, for example, the 36" ballast (for the 33" lamp), and can be designed as 1-24" lamp/2-24" lamps/1-36" lamp/2-36" lamps/1-48" lamp/2-48" lamps. An additional 6 ballast that fit the above description also fit the worldwide market ballast description which automatically can recognize current between 120V–240V. As well known to those skilled in the art, ballast size and type can be matched to the lamp size and type.

Current flowing into purification device 1 from the main power source goes to control relay 2 to which a momentary contact safety switch 4 is coupled. Safety switch 4 is designed to cut off power to UV lamps 18 to prevent inadvertent exposure of an individual to ultraviolet radiation. For example, safety switch 4 may be installed on a door allowing access to the UV lamps (i.e. an existing access door or optional Plexiglas door 28) to shut off the system if the door is opened, thereby ensuring the safety of maintenance or other personnel.

From control relay 2, the power goes to suppressor 6. Suppressor 6 suppresses any initial electrical surge, to avoid burning out expensive lamps. From suppressor 6, the system is wired to terminal strips 8. Terminal strips 8 are electrically coupled to the input of adjacent ballasts 10. This electrically ties all ballasts together which are together tied, again electrically, to the suppressor. As a result, the individual lamps 18 are electrically protected from the initial electrical surge each time the device is turned on.

The output side of the ballasts are coupled to terminal strip 20. From terminal strip 20, a first set of wires are coupled to power LED indicator lights 22 which indicate that each individual ballast and lamp has electricity going to it. Also, from terminal strip 20, a second set of wires 24 are used to couple terminal strip 20 to one or more four pin lamp connectors 26, which are fastened or otherwise mounted onto the interior of the air conveyance system. UV lamp 18 is mounted into each connector 26 and multi-faceted tin reflector 30 is placed at either end of the lamp.

As depicted in FIG. 1, each UV lamp 18 has four male pins and pushes straight into four cavities in four pin (female) connector 26. Each lamp 18 is illuminated entirely from one end. The lamps are supported in an appropriate manner. With the exception of four pin connectors 26, lamps 18 and multi-faceted tin reflectors 30, may be installed separately from the air conveyance system. For instance, the unit may be installed free-standing on free-standing unit 40. Stand 40 may be made of aluminum and have a first vertical portion 44 for supporting the electrical components and a second horizontal portion 46 for fastening into the floor. This portion of the invention is installed outside of the air conveyance system to reduce vibration on the electrical parts and thus avoids the needles restriction of air flow in the air conveyance system. The main parts of the system that can be installed in the air handler is the UV lamps.

In any of the embodiments described herein, an aluminum or marine grade polymer cover may be provided to cover the electrical components. If an access door is needed, a door, such as door 28, which is preferably Plexiglas with hinges 27, latch 29 and safety switch 4, maybe installed. No holes need to be cut into the air conveyance system. The wires feeding pin connectors 26 require only a small hole. Reflective tape may be placed on any parts of the device that are plastic that will be exposed to ultraviolet radiation for UV and general protection.

Figure 2A:
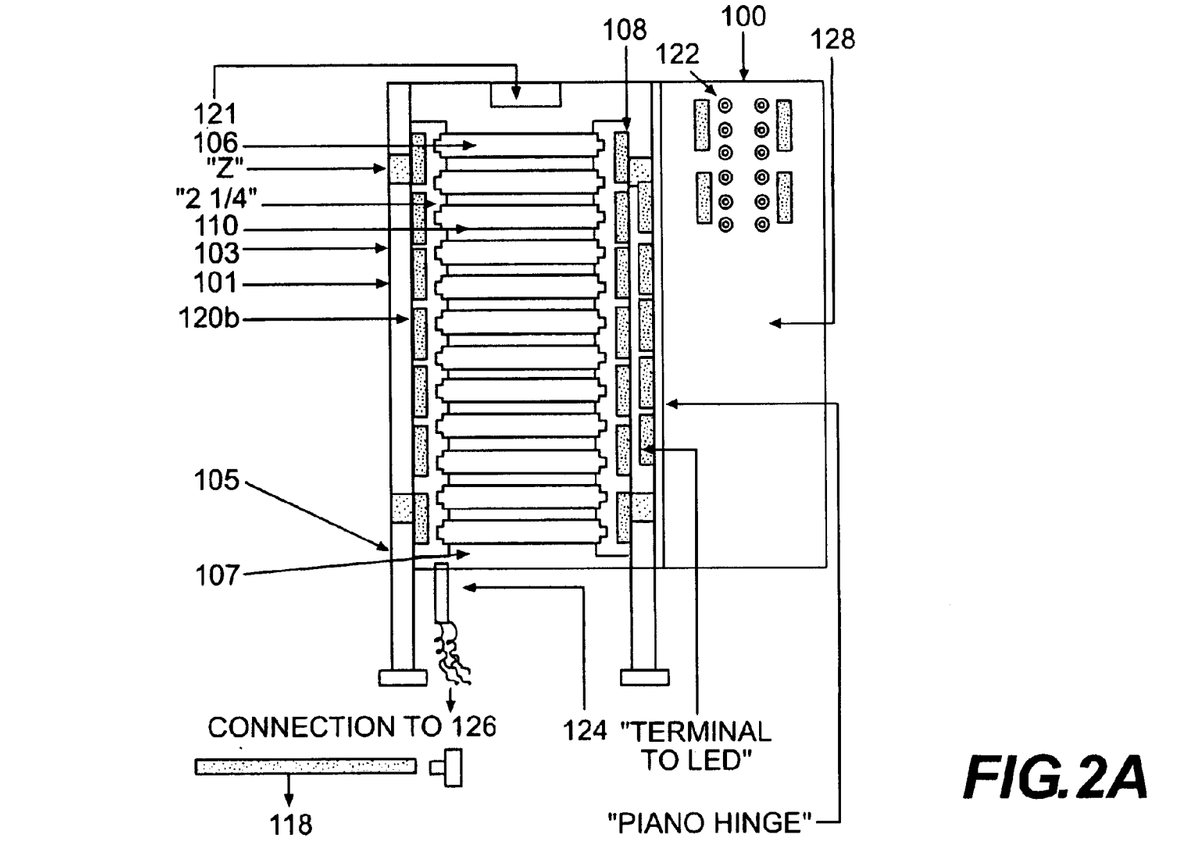
Figure 2B:
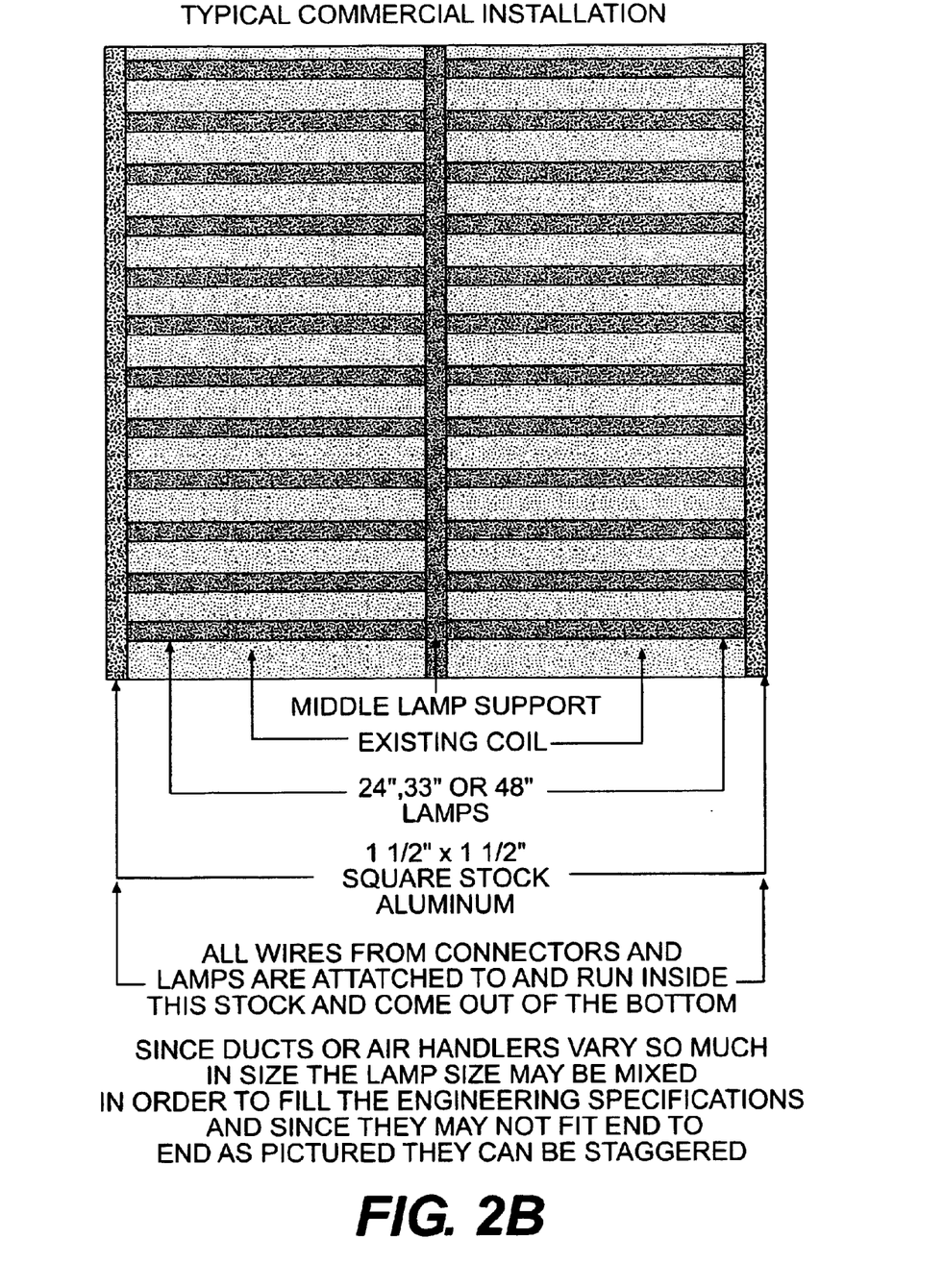

Another embodiment of the invention, particularly useful in a commercial application, is depicted in FIG. 2. Referring to FIG. 2a, purification apparatus 100 has a housing 101 comprising box 103 having door 128 and legs 105. Legs 105 have openings 107 disposed to allow air flow. Box 103 and door 128 are preferably made of solid UV resistant polymer sheets, approximately ½" thick. Legs 105 are preferably made of 1½" by 1½" aluminum. As noted on FIG. 2, the Z strips are located in four places attached to the legs to support the vertically placed 2¼" flat aluminum which ultimately supports the ballasts. Door 128 is mounted via hinges on box 103 so as to cover opening 107 in box 103. Suppressor 106, terminal strips 120a and 120b and ballasts 110 are preferably disposed inside box 103. Box 103 preferably has an inlet and outlet, which may be disposed on its upper and lower sides, respectively, and an exhaust fan 121 disposed near the upper outlet to evacuate heat from the interior of box 103. The inlet and outlet may, if desired, comprise a plurality of heat escape holes. The lower outlet may have an open bottom or a closed bottom with fresh air intake holes to facilitate air flow to the top of the unit in which heat from the ballasts escapes and is pulled by means of a fan installed at the top. There do not need to be additional holes installed in the top for heat removal, just the fan will suffice. In the residential unit, a fan may not be included so holes can be in the top and bottom of the box which holds the ballast thus using the natural rise of hot air to cool the ballast. A typical commercial instillation of lamps is shown in FIG. 2b.

Figure 3A:
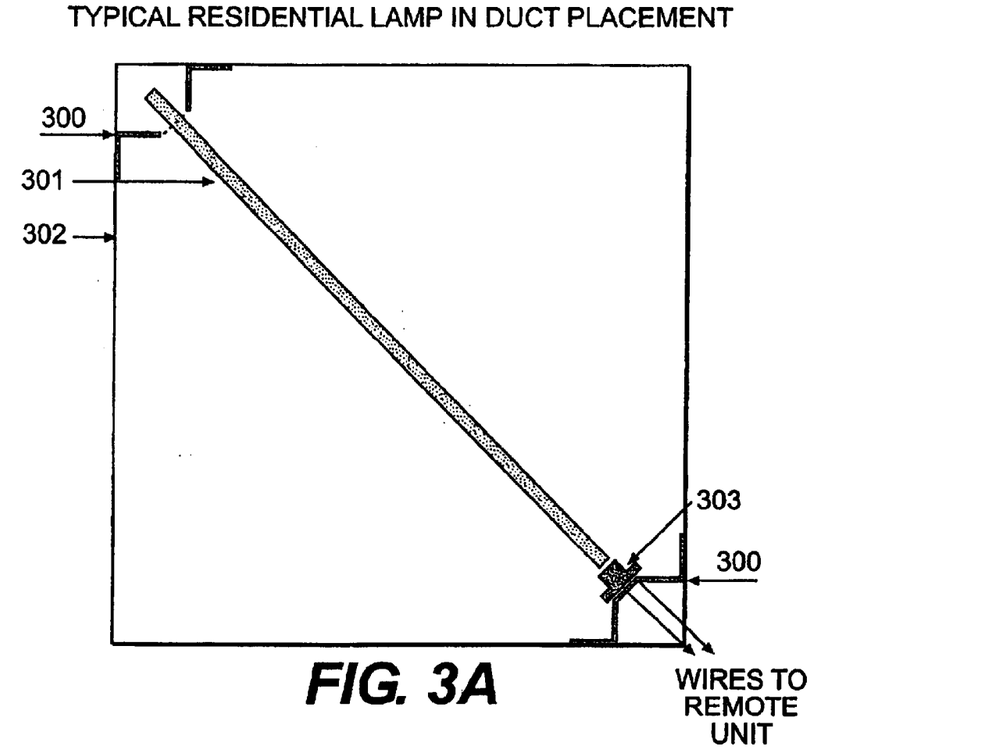
Figure 3B:
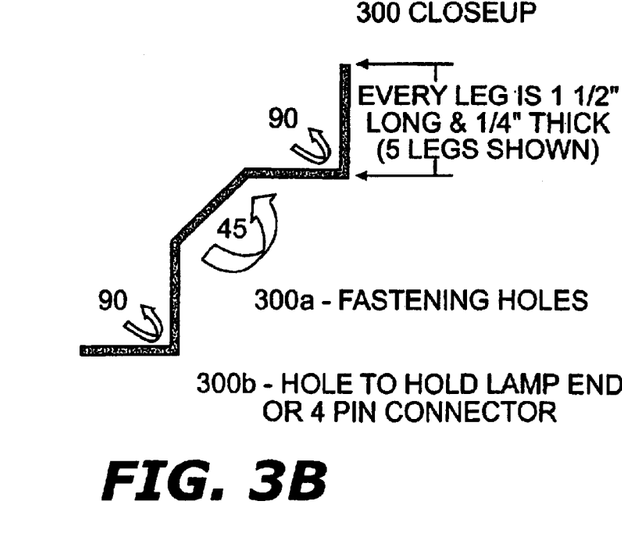
Figure 3C:
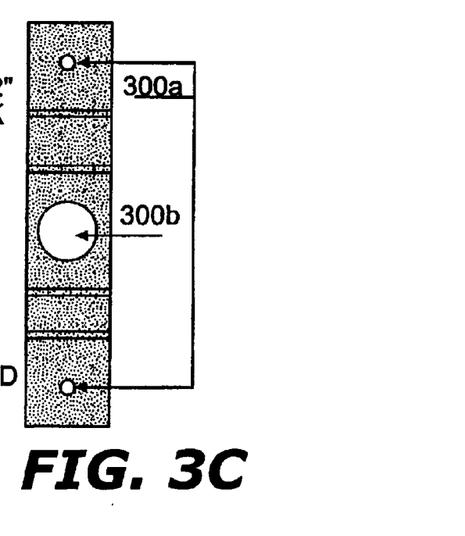

In operation, power from the main power source flows to suppressor 106. Suppressor 106, which is generally used with 16 or more ballasts (which are usually coupled back to back), is coupled to terminal strips 108. Terminal strips 108 connect the hot and neutral from the main electric to the ballast wires. Terminal strips 108 are coupled to a plurality of ballasts 110 and ballasts 110 are coupled to terminal strips 120a and 120b. Terminal strips 120a are used to connect ballasts 110 to LED lights 122. Terminal strips 120b are connected to four pin connectors 126 via wires 124 and wires 124 are preferably 14 gauge wires. Thus, terminal strips 120b and wires 124 connect ballasts 110 to four pin connectors 126 and UV lamps 118. As with the previous embodiment, wires 124 are preferably of sufficient length that UV lamps 118 and connectors 126 may be mounted inside a duct of an air conditioning system, remote from the rest of the electrical components. Connectors 126 are preferably disposed in a lamp holder 130. A preferred embodiment of lamp holder 300 is depicted in FIG. 3 which shows placement of a residential lamp in a duct having a plurality of four pin (female) connectors 126 adapted to mate with four pin UV bulbs 118 disposed in linear fashion in lamp holder 300. Preferred UV lamps are four pin circline base single-ended UV lamps which may be selected from at least three sizes for a germicidal lamp and three sizes for a high output germicidal lamp with the following specifications: Standard ~24" arc~20.75, lamp watts~30, current ~425 mA V@60 Hz ~85 uw/cm$^2$~99; High out ~24" arc~20.75, lamp watts~60, current ~800 mA V@60 Hz ~92 uw/cm$^2$~192; Standard ~36" arc~30.00, lamp watts~39, current ~425 mA, V@60 Hz ~112 uw/cm$^2$~140; High out ~36" arc~30.00, lamp watts~80 current ~800 mA V@60 Hz ~124 uw/cm$^2$~252; Standard ~48" arc~45.2, lamp watts~60, current ~425 mA V@60 Hz ~170 uw/cm$^2$~212; and High out~48" arc~45.2, lamp watts~114, current ~800 mA, V@60 Hz ~182 uw/cm$^2$~321. Lamp holder 130 is then mounted inside a duct of an air conditioning system.

Typical installation for the most effective cleaning of the coil and the air would be within one foot of the coil. Lamps are placed parallel to the cooling coil either in a horizontal, vertical or angled configuration. Lamps placed in this position maintain a better general cleanliness and thus are more efficient. Lamps can also be placed after the filters which tends to be more effective at this point which is where the air is moving the slowest. Also, the UV-C ray has been proven to be highly effective when placed near a reflective aluminum surface such as a cooling coil.

Figure 4A:
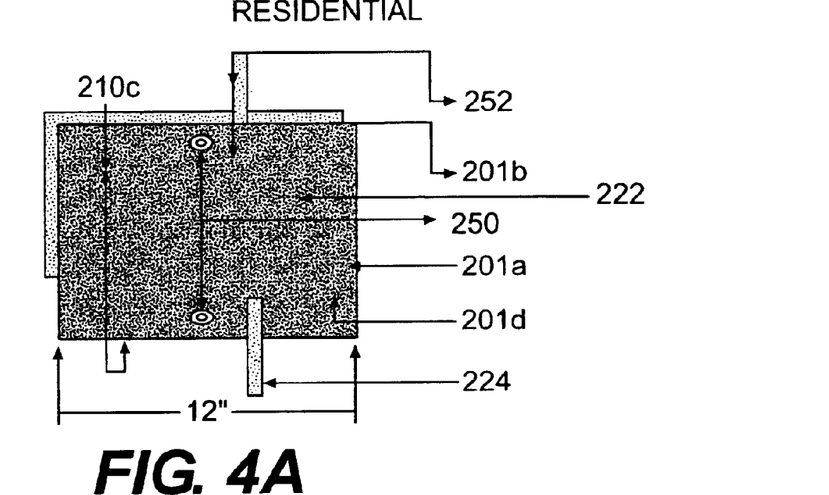
Figure 4B:
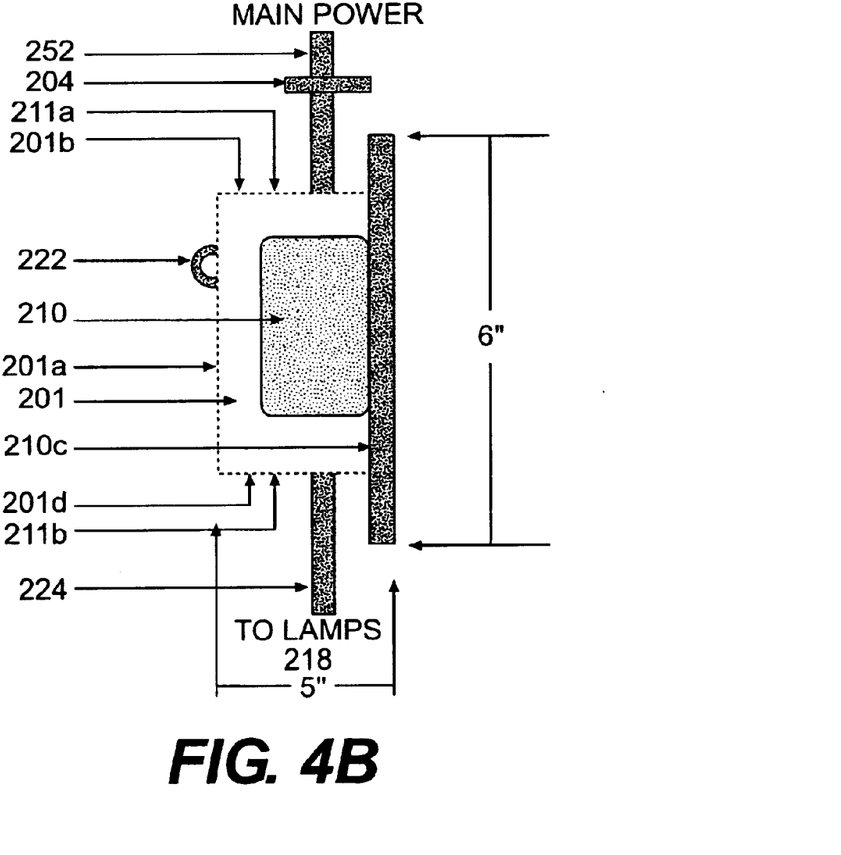

FIG. 4 depicts another embodiment of a purification device according to the invention particularly useful in residential settings. There are a few items that are not needed in the residential unit such as a suppresser ballast, a ballast stand, terminal strips and fan. In addition, some components in the residential unit may be different than in the commercial unit such as, for example, the bulb holder. Also available, especially in the case of residential units that have a plastic drain pan under the air conditioning coils, is an aluminum metal (in a rolled sheet form) at 0.019" thickness to insure the ability to conform to the custom needs of each application to the drain pan or other interior duct surfaces. This sheet aluminum can be applied to the interior of the duct or air handler area for reflective purposes using large headed pop rivets or regular rivets with washers. In the area of the drain pan the aluminum can be fastened marine grade glue and sealed with a marine grade silicone.

Referring to FIGS. 4a-b, air purification system 200 comprises a housing 201 enclosing a ballast 210. Ballast 210 is coupled to LED readout 222 mounted on the front 201a of housing 201. Ballast 210 is also coupled via wire 224 to UV lamp 218. Lamp 218 is disposed inside the duct of an air conditioning system. Housing 201 has heat outlet or escape holes 211a disposed in housing top 201b and air flow or inlet holes 211b disposed in housing bottom 201d, to allow ventilation of heat from the system. Since UV is known to have a degradation effect on plastic, reflective tape may be included to cover any wires that will be potentially exposed to the UV rays. The supplied metal tape may be used also to apply to plastic fan blades commonly found in p-tech type air conditioning systems. Ballast 210 is mounted inside housing 201 on the back 210c of housing 210. Back 201c preferably comprises a ½" polymer sheet that extends above and below the top 201b and bottom 201d of housing 210. Fastening holes 250 are provided in back 210c to allow it to be easily mounted on a nearby wall, truss. Power is supplied to ballast 210 via Romex 252 (a type flexible electrical conduit). From ballast 210, power flows via wires 224 to the UV lamp 218, and a safety switch 204 is connected. This invention embodies a ballast for each of the above lamps that powers 2 lamps per ballast this is improved from other type applications for 2 reasons: First, most conventional units simply place a non-engineered amount of UV in the duct system. With this method, engineered for example according to the Westinghouse formula, it is possible to provide sufficient UV and at a cost effective rate because of being able to provide double the normal amount of lamps. Also, most conventional units are only place on one side of the coil, with this embodiment, it is possible to place one lamp per side thus insuring the cleanliness of both sides of the coil.

As will be clear to those of skill in the art, various safety switches may be used to prevent an individual from being exposed to the UV lamps while they are illuminated. One useful safety switch for commercial use is known as a door jamb light switch. It can be installed on an access door to a duct or an air handler blower door. When the door is closed, the switch is in an open position that allows current to flow to the UV lamps. Another useful type of switch for use in a residential setting is safety switch. This type of switch may be a doorbell-type switch that would operate the UV lamps for as long as the switch is depressed or the access door is closed. Thus, when the access door is opened, the safety switch turns off the UV lamps. In a similar configuration, the safety switch may be a micro-switch.

Figure 5:
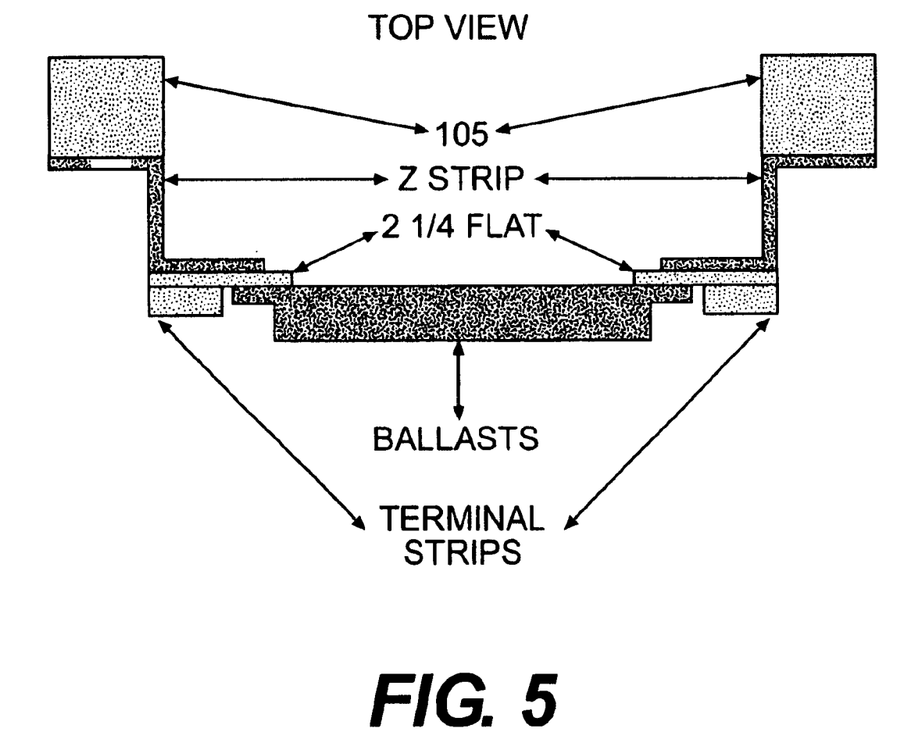
FIG. 5 is a side view showing placement of ballasts.

The residential apparatus preferably comprises connecting means, such as a plug or direct wiring, for connecting the apparatus to a main power source or supply, a suppressor ballast coupled to the connecting means for suppressing any electrical surge when the apparatus is activated, a plurality of fluorescent light ballasts (a suppressor is generally used when using 16 or more light ballasts) coupled to the suppressor ballast, the fluorescent light ballast configured to convert 60 hertz to 20–100 kilohertz; at least one electrical connector, coupled to the fluorescent light ballast and adapted to receive a UV-C lamp, means for de-energizing the lamp in response to a signal change, and indicator means for indicating when the lamp is energized. Ballast placement is shown in FIG. 5. Preferably, the electrical connector is coupled to the fluorescent light ballast via coupling means, for example, a length of wire, so that, if desired, the electrical connector and UV lamps may be disposed inside a duct of the air conditioning system, remote from the connecting means, the suppressor ballast and the fluorescent light ballast.

Preferably, the fluorescent light ballast and the suppressor ballast are disposed in a box-shaped housing. The housing may comprise mounting means for mounting the housing on a flat surface, such as small holes on a back side to allow it to be screwed or nailed to a wall. The housing also may have holes or openings on its upper and lower sides to provide ventilation. This embodiment is particularly useful in a residential air conditioning system, but may be used in other systems as desired.

Another commercial apparatus comprising a control relay, a suppressor ballast coupled to the control relay for suppressing any electrical surge when the apparatus is activated, a plurality of fluorescent light ballasts coupled to the suppressor ballast, the fluorescent light ballasts configured to convert 60 hertz 20 to 20–100 kilohertz, a plurality of four pin electrical connectors, wherein each of the plurality of four pin electrical connectors is coupled to one of the plurality of fluorescent light ballasts and is adapted to receive a UV-C lamp, means for de-energizing the lamps in response to a signal change, and indicator means for indicating when one or more of the plurality of lamps is energized. The four pin electrical connectors are preferably coupled to the fluorescent light ballasts via coupling means of sufficient length that the four pin electrical connectors and UV lamps may be disposed inside an air conditioning duct, remote from the control relay, the suppressor ballast and the fluorescent light ballasts.

Figure 6:
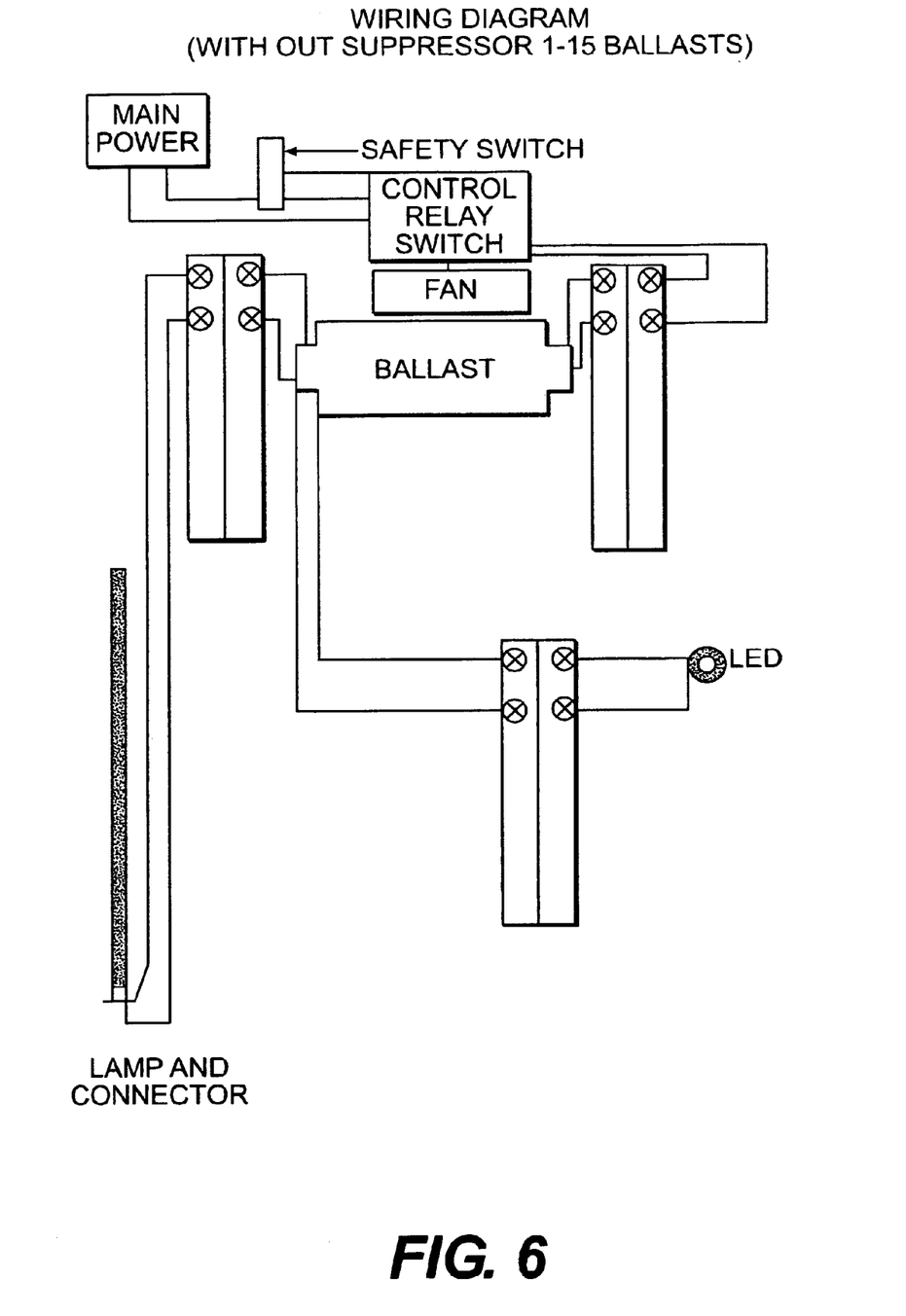
FIG. 6 is wiring diagram which does not include a suppressor.
Figure 7:
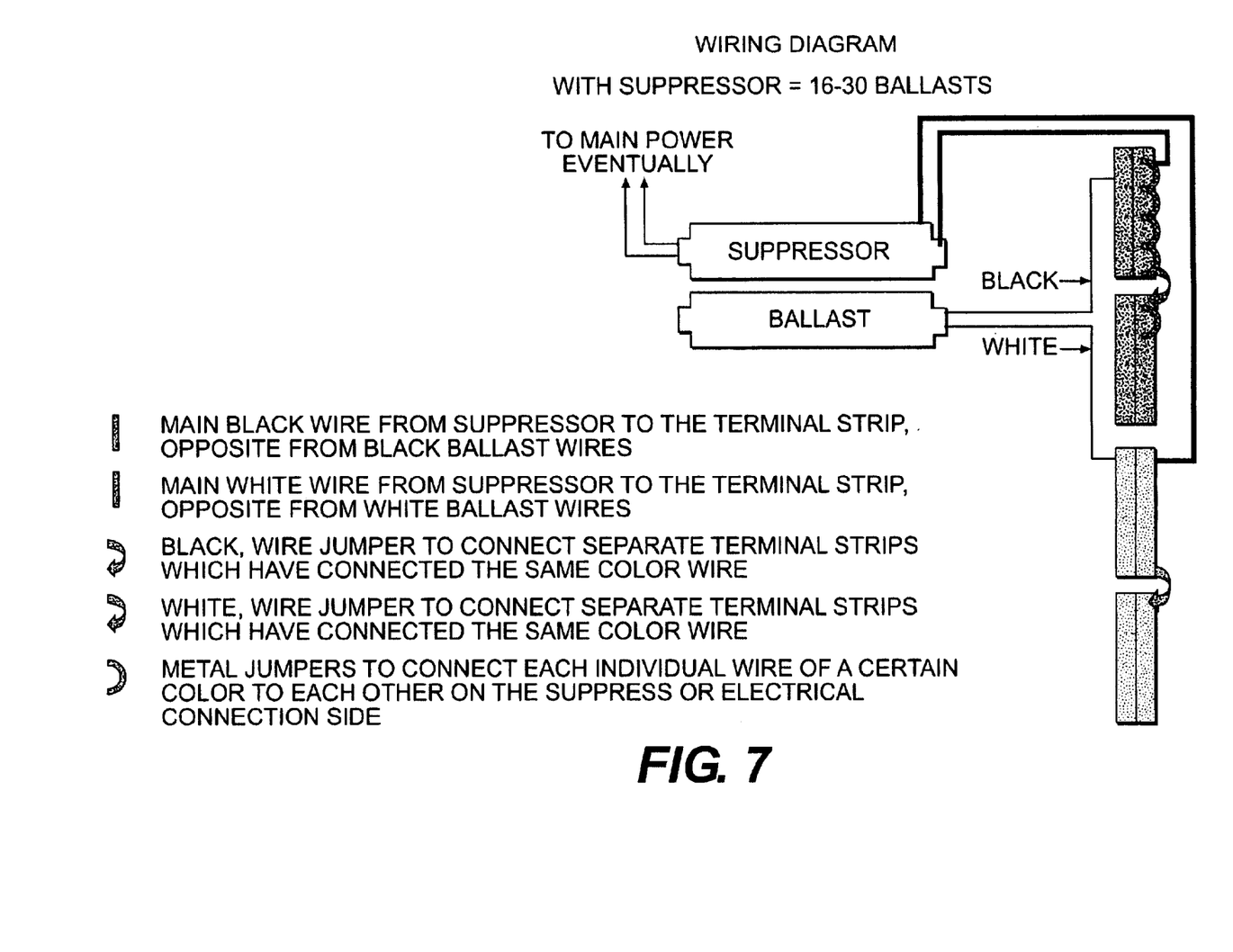
FIG. 7 is a wiring diagram which includes a suppressor.

The apparatus may further comprise a plurality of UV-C lamps designed for mating with the four pin electrical connectors and a plurality of reflectors arranged so that a reflector is disposed at least one end of each lamp. The connectors, lamps and reflectors are preferably disposed inside the duct such that the reflectors spin as air flows through the duct. Preferred reflectors include a reflectivity kit (paint or aluminum to increase reflectance 200% or more). Fluorescent light ballasts may be 40V to 220V, and preferably 85V to 182V. More preferably, the fluorescent light ballasts are 220 volt ballasts such as solid state ballasts. The indicator means preferably comprises an LED indicator light coupled to each of the fluorescent light ballasts to indicate whether power is going to each of the fluorescent light ballasts. A wiring diagram without a suppressor is shown in FIG. 6 and a wiring diagram with a suppressor is shown in FIG. 7.

To protect individuals from exposure to the UV lamps in the air conditioning duct, in one embodiment, a door, such as a Plexiglas door, is disposed on the duct and a safety switch comprising a doorjamb light switch is disposed on the door such that it is actuated when the door is opened. This door and safety switch allow access to the lamps while protecting individuals from UV exposure. Alternately, the safety switch may comprise a switch that allows the UV lamps to be energized so long as the switch is depressed or the door is closed. In still other embodiments, the switch may be a micro-switch or a momentary contact safety switch.

In a preferred embodiment, the four pin electrical connectors, the UV-C lamps and the reflectors are disposed inside a duct of the air conditioner, and the control relay, the suppressor ballast and the plurality of fluorescent light ballasts are disposed remotely from the air conditioning system. For example, the control relay, suppressor ballast and fluorescent light ballasts may be enclosed in a cover, such as an aluminum cover, and mounted on a nearby wall, or on a free-standing stand. This protects these components from unnecessary vibration from the system. The cover preferably has an inlet and an outlet and an exhaust fan disposed inside the cover near the outlet to exhaust heat from inside the cover. Alternately, the four pin electrical connectors, the UV-C lamps, the reflectors, the control relay, the suppressor ballast and the plurality of fluorescent light ballasts may all be disposed inside the air conditioning system. As is clear to those of skill in the art, this embodiment can be incorporated into air handling systems of any type, but is particularly useful for commercial air handling systems.

Another embodiment of the invention is directed to a kit for a customized air purification device comprising a cover, a control relay, a safety switch, a suppressor ballast, a plurality of fluorescent lamp ballasts, a plurality of terminal strips, a plurality of LED indicator lights, a plurality of four pin electrical connectors, and one or more components selected from the group consisting of a plurality of UV-C lamps, a plurality of connecting wires, a plurality of multi-faceted tin reflectors, a reflective tape, a free-standing stand, a plurality of self tapping aluminum screws, a plurality of UV-C lamps, a plurality of concrete screws and a Plexiglas door. Preferably, the cover comprises a custom aluminum cover and the safety switch comprises a momentary contact safety switch. The kit can be incorporated into air handling systems of any type, but is particularly useful in customizing a commercial air conditioning system.

In one embodiment of the kit, aluminum coil stock and fastening means may be provided in the kit to enhance reflection around the UV-C lamps. This aluminum coil stock can be rolled out, and cut to fit and installed in the portion of the duct surrounding the UV-C lamps. Suitable fastening means for affixing the aluminum coil include, but are not limited to, spray contact cement and a rivet/grommet combination.

Another embodiment of the invention is directed to a method for killing microorganisms in an air conditioning system having at least one duct for the passage of air therethrough, the method comprising providing connecting means for connecting to a main power source, providing an optional suppressor ballast coupled to the connecting means for suppressing any electrical surge when the apparatus is activated, providing a fluorescent light ballast coupled to the suppressor ballast, the fluorescent light ballast configured to convert 60 hertz to 20–100 kilohertz, providing an electrical connector, coupled to the fluorescent light ballast and adapted to receive one or more UV-C lamps, and wherein the electrical connector is coupled to the fluorescent light ballast via coupling means such that the electrical connector may be disposed remote from the connecting means, the suppressor ballast and the fluorescent light ballast, providing means for de-energizing the lamp in response to a signal change, and providing indicator means for indicating when the lamp is energized. The method may further comprise providing a housing for the fluorescent light ballast and the suppressor ballast. The housing preferably has mounting means for mounting the housing on a flat surface and holes in the housing to provide ventilation. This method is useful for treating both residential and commercial air conditioning systems.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. An apparatus for killing microorganisms in an air conditioning system, said air conditioning system having at least one duct for the passage of air therethrough, said apparatus comprising:
   a first connector for connecting said apparatus to a main power source;
   a fluorescent light ballast configured to convert 60 hertz to 20–100 kilohertz;
   a second connector located in a duct of the air conditioning system adapted to receive a UV-C lamp, wherein said second connector is coupled to said fluorescent light ballast via a coupler such that the first connecting means and said fluorescent light ballast is remote from the duct of the air conditioning system; and
   a reflector disposed within the at least one duct that spins as air flows through said duct.

2. The apparatus of claim 1, further comprising a suppressor ballast coupled to said first connector for suppressing any electrical surge when the apparatus is activated.

3. The apparatus of claim 2, wherein the fluorescent light ballast and said suppressor ballast are disposed in a housing, said housing comprising a mounting for mounting said housing on a flat surface and wherein said housing has holes therethrough to provide ventilation.

4. The apparatus of claim 1, wherein the air conditioning system is a residential air conditioning system.

5. The apparatus of claim 1, further comprising de-energizing the lamp in response to a signal change and an indicator for indicating when the lamp is energized.

6. An apparatus for killing microorganisms in an air conditioning system, said air conditioning system having at least one duct for the passage of air therethrough, said apparatus comprising:
   a control relay;
   a plurality of fluorescent light ballasts configured to convert 60 hertz to 20–100 kilohertz;
   a reflector disposed in said at least one duct that spins as air flows through; and
   a plurality of electrical connectors located in the duct of the air conditioning system, wherein each of said plurality of electrical connectors is coupled to one of said plurality of fluorescent light ballasts and is adapted to receive a UV-C lamp, and said electrical connectors are coupled to said fluorescent light ballasts via couplers such that the control relay and said fluorescent light ballasts are remote from the duct of the air conditioning system.

7. The apparatus of claim 6, further comprising a suppressor ballast coupled to said control relay for suppressing any electrical surge when the apparatus is activated.

8. The apparatus of claim 6, further comprising a plurality of UV-C lamps designed for mating with said electrical connectors and a plurality of reflectors arranged so that one of said plurality of reflectors is disposed at least one end of each of said plurality of lamps.

9. The apparatus of claim 6, wherein the reflector comprises a plurality of reflectors disposed in said duct, and wherein said plurality of reflectors spin as air flows through said duct.

10. The apparatus of claim 6, wherein the fluorescent light ballasts are 220 volt ballasts.

11. The apparatus of claims 6, further comprising:
    a de-energizer for de-energizing the lamps in response to a signal change and an indicator for indicating when one or more of the plurality of lamps are energized.

12. The apparatus of claim 11, wherein the indicator comprises an LED indicator light coupled to each one of said plurality of fluorescent light ballasts to indicate whether power is going to each of said fluorescent light ballasts.

13. The apparatus of claim 6, further comprising a safety switch operatively coupled to said control relay.

14. The apparatus of claim 13, wherein the UV-C lamps are disposed inside said duct, and a door is disposed on said duct to allow access to said lamps and wherein said safety switch comprises a door jamb light switch which is actuated when said door is opened.

15. The apparatus of claim 13, wherein the UV-C lamps are disposed inside said duct, and a door is disposed on said duct to allow access to said lamps and wherein said safety switch comprises a switch that allows the UV-C lamps to be energized so long as the safety switch is depressed or the door is closed.

16. The apparatus of claim 13, wherein the safety switch comprises a micro-switch.

17. The apparatus of claim 13, wherein the safety switch comprises a momentary contact safety switch.

18. The apparatus of claim 8, wherein said UV-C lamps and said reflectors are disposed inside said duct and said control relay and said plurality of fluorescent light ballasts are disposed remotely from said air conditioning system.

19. The apparatus of claim 8, wherein said UV-C lamps, said reflectors said control relay and said plurality of fluorescent light ballasts are disposed inside the air conditioning system.

20. The apparatus of claim 6, further comprising an aluminum cover.

21. The apparatus of claim 6, wherein the air conditioning system is a commercial air conditioning system.

22. The apparatus of claim 6, further comprising an exhaust fan.

23. A method for killing microorganisms in an air conditioning system, said air conditioning system having at least one duct for the passage of air therethrough, said method comprising:

providing a first connector for connecting to a main power source;

providing a fluorescent light ballast coupled to said suppressor ballast, said fluorescent light ballast configured to convert 60 hertz to 20–100 kilohertz;

providing a reflector located within the at least one duct of the air conditioning system, wherein said reflector spins as air flows through said at least one duct; and providing a second connector located in a the at least one duct of the air conditioning system adapted to receive a UV-C lamp, wherein said second connector is coupled to said fluorescent light ballast via a coupler such that the first connecting means and said fluorescent light ballast is remote from the duct of the air conditioning system and wherein said ballast is not subjected to all of the vibrations of the air conditioning system.

24. The method of claim 23, further comprising:

providing for de-energizing the lamp in response to a signal change; and providing an indicator for indicating when the lamp is energized.

25. The method of claim 23, further comprising providing a suppressor ballast coupled to said first connector for suppressing any electrical surge when the apparatus is activated.

26. The method of claim 23, further comprising providing a housing, wherein said fluorescent light ballast is disposed in said housing, said housing comprising a mounting for mounting said housing on a flat surface and wherein said housing has holes therethrough to provide ventilation.

27. The method of claim 23, wherein the air conditioning system is a residential air conditioning system.

28. The method of claim 23, wherein the air conditioning system is a commercial air conditioning system.

29. An apparatus for cleaning air in an air conditioning system, said air conditioning system having at least one cooling coil and at least one duct, said apparatus comprising:

a fluorescent light ballast;

a first UV-C lamp connected to the fluorescent light ballast and located on a first side of the cooling coil in said air conditioning system;

a reflector located within the at least one duct of the air conditioning system, wherein said reflector spins as air flows through said at least one duct; and a second UV-C lamp connected to the fluorescent light ballast and located on a second side of the cooling coil in said air conditioning system.

30. The apparatus of claim 29, wherein the fluorescent light ballast is located remotely from the duct and said ballast is not subjected to all of the vibrations of the air conditioning system.

31. The apparatus of claim 29, further comprising a suppressor ballast coupled to the fluorescent light ballast for suppressing any electrical surge when the apparatus is activated.

32. The apparatus of claim 31, wherein the fluorescent light ballast and said suppressor ballast are disposed in a housing, said housing comprising a mounting for mounting said housing on a flat surface and wherein said housing has holes therethrough to provide ventilation.

33. The apparatus of claim 29, wherein the air conditioning system is a residential air conditioning system.

34. The apparatus of claim 29, further comprising de-energizing the lamp in response to a signal change and an indicator for indicating when the lamp is energized.

35. An apparatus for cleaning air in an air conditioning system, said air conditioning system having at least one cooling coil and at least one duct, said apparatus comprising:

a fluorescent light ballast;

at least one UV-C lamp connected to the fluorescent light ballast for cleaning the entire cooling coil in said air conditioning system; and a reflector disposed in said at least one duct that spin as air flows through the duct.

36. The apparatus of claim 35, wherein the fluorescent light ballast is located remotely from the duct and wherein said ballast is not subjected to all of the vibrations of said air conditioning system.

37. The apparatus of claim 35, further comprising a suppressor ballast coupled to the fluorescent light ballast for suppressing any electrical surge when the apparatus is activated.

38. The apparatus of claim 37, wherein the fluorescent light ballast and said suppressor ballast are disposed in a housing, said housing comprising a mounting for mounting said housing on a flat surface and wherein said housing has holes therethrough to provide ventilation.

39. The apparatus of claim 35, wherein the air conditioning system is a residential air conditioning system.

40. The apparatus of claim 35, further comprising de-energizing the lamp in response to a signal change and an indicator for indicating when the lamp is energized.

41. The apparatus of claim 1, wherein the ballast is not subjected to all of the vibrations of the air conditioning system.

42. The apparatus of claim 1, wherein the ballasts are not subjected to all of the vibrations of the air conditioning system.

* * * * *